US011779389B2

(12) United States Patent
Kim (10) Patent No.: US 11,779,389 B2
(45) Date of Patent: Oct. 10, 2023

(54) SKIN TREATMENT DEVICE (71) Applicant: ILOODA Co., Ltd., Suwon-si (KR)

(72) Inventor: Yong Han Kim, Suwon-si (KR)

(73) Assignee: ILOODA Co., Ltd., Suwon-si (KR)

( * ) Notice: Subject to any disclaimer, the term of this patent is extended or adjusted under 35 U.S.C. 154(b) by 287 days.

(21) Appl. No.: 17/458,577

(22) Filed: Aug. 27, 2021

(65) Prior Publication Data

US 2023/0065052 A1  Mar. 2, 2023

(51) Int. Cl.
*A61B 18/14* (2006.01)
*A61B 18/00* (2006.01)

(52) U.S. Cl.
CPC .......... *A61B 18/1477* (2013.01); *A61B 2018/00452* (2013.01); *A61B 2018/00589* (2013.01)

(58) Field of Classification Search
CPC ............ A61B 18/1402; A61B 18/1477; A61B 2018/0016; A61B 2018/00178; A61B 2018/0196; A61B 2018/00452; A61B 2018/0047; A61B 2018/00589; A61B 2018/143; A61B 2018/1467; A61B 2018/1475; A61N 1/06; A61N 1/328
USPC ..................................... 606/41–50
See application file for complete search history.

(56) References Cited

U.S. PATENT DOCUMENTS

| 6,277,116 | B1 | 8/2001 | Utely et al. |
| 6,628,990 | B1 | 9/2003 | Habib et al. |
| 7,278,991 | B2 * | 10/2007 | Morris ............... A61B 18/1477 606/41 |
| 7,824,394 | B2 * | 11/2010 | Manstein ........... A61B 18/1477 606/49 |
| 9,095,357 | B2 | 8/2015 | Manstein |
| 9,510,899 | B2 | 12/2016 | Manstein |
| 11,344,363 | B2 * | 5/2022 | Ko .......................... A61N 1/05 |
| 2002/0120260 | A1 | 8/2002 | Morris et al. |
| 2002/0128641 | A1 | 9/2002 | Underwood et al. |
| 2005/0222565 | A1 | 10/2005 | Manstein |
| 2014/0194789 | A1 * | 7/2014 | Ko ........................ A61N 1/328 601/18 |
| 2022/0072299 | A1 * | 3/2022 | Ko ..................... A61N 1/36017 |

* cited by examiner

*Primary Examiner* — Michael F Peffley
(74) *Attorney, Agent, or Firm* — Revolution IP, PLLC (57) ABSTRACT

The present invention relates to a skin treatment device including a handpiece and a needle tip enabling to be coupled to the handpiece, wherein as the needle tip is mounted on the distal end of the handpiece, electrical connection with the handpiece can be made stably, and even if the needle module built in the needle tip performs linear reciprocating motions of extension and retraction by the driving device provided in the handpiece, the motion trackable connector provided in the needle tip can stably keep the electrical connection between the handpiece and the needle tip.

10 Claims, 11 Drawing Sheets

SKIN TREATMENT DEVICE

BACKGROUND OF THE INVENTION

Field of the Invention

The present invention relates to a skin treatment device for transfer radio frequency energy to dermal tissues using micro-needles, which is configured to obtain skin care and anti-aging effects by coagulating tissues in the specific region using micro-needles and regenerating a new collagen at the coagulated tissues.

Description of the Related Art

The skin of the human body consists of epidermis, dermis, and subcutaneous fat layers, which are connected to the base layer and are jelly-like in moisture, protein, sugars, minerals, and so on.

The dermal layer of the skin consists of capillaries associated with blood circulation while nourishing the epidermal layer, papillae layer in which lymph transporting lymph is located, and delusional layer which consists of collagen, collagenous fibers associated with wrinkles on the skin, elastin that is a resilient fiber giving skin elasticity and substrate.

For skin beauty, such as preventing aging of the skin, it is necessary to supply beneficial substances to the dermis as described above or to generate new collagens in the dermis. A method for using micro-needles is widely used as an effective treatment method for skin care.

The method using the micro-needles, by inserting a plurality of the micro-needles into the dermal layer of the skin and applying radio frequency energy to the dermal tissue, forms coagulation regions in a specific area of the dermal tissue, and then induces the production of new collagen in the dermal layer.

For instance, a number of prior arts such as US 2005-0222565, U.S. Pat. Nos. 9,095,357, 9,510,899, 6,277,116, US 2002-0128641 are disclosing devices and methods for inserting a plurality of the micro-needles into the dermal layer of the skin and then transferring RF energy through the micro-needles to the dermal tissue.

These micro-needle skin treatment devices may include a hand-held handpiece and a tip module enabling to be coupled to the end of the handpiece.

The tip module contains a plurality of the modularized micro-needles, which can be configured to be directly driven by a drive such as a solenoid in the handpiece so that the micro-needles are extended out of the tip module and retreated back into the tip module.

When the end of the tip module is in contact with the patient's skin and a solenoid in the handpiece is operated, the micro-needles are extended from the tip module and inserted into the skin, and RF energy is applied to the tissue in the skin through the micro-needles to form coagulation regions.

As such, the technology related to RF energy transferring through needles driving to be extended and retracted by solenoid-like drive devices is disclosing prior arts such as U.S. Pat. No. 6,628,990, US 2002-0120260.

However, the prior arts as described above are related to cases where the handpiece and tip are not distinct and consist of an integral application.

However, one tip module cannot be used for multiple patients because the micro-needles used for skin treatment devices as described above are inserted into the skin of the human body. If a tip module is used for one patient, another tip module should be used for the other patient (the existing tip module for one patient must be discarded).

Accordingly, the tip module should be removable from the end of the handpiece in a skin treatment device using micro-needles as described above.

As the tip module is coupled at the end of the handpiece, an electrical connection must be made so that RF electrical signals can be transmitted from the external RF source connected to the handpiece to the micro-needles, while a module of the micro-needles installed inside the tip module is capable of straight reciprocating extension and retraction.

SUMMARY OF THE INVENTION

The present invention relates to a skin treatment device comprising a handpiece, a needle tip and a motion trackable connector. The handpiece is configured to include a motor to move a driving shaft linearly therein and having a distal end from which the driving shaft is protruded, wherein a connector to tip is provided on the distal end.

The needle tip is configured to comprise a tip body, a needle module and a connecting board. The tip body is configured to be detachably coupled to the distal end of the handpiece and have needle-holes through which a plurality of needles move. The needle module includes a needle board coupled to the driving shaft and the plurality of needles electrically connected to the needle board, wherein the needle module linearly moves by the driving shaft for the needles to be extended and retracted through the needle-holes. The connecting board has connecting conductors to electrically contact with the connector to tip of the handpiece by coupling with the tip body and the distal end of the handpiece.

The motion trackable connector is configured to electrically connect with the connecting board and the needle module so that RF energy delivers from the connecting board to the needle module, and keep the electrically connection trackable to motion of the needle module during extension and retraction of the needles.

Preferably, the connecting board includes a through hole through which the driving shaft passes and is coupled to the needle module.

Preferably, the skin treatment device further comprises a tip data storage on the connecting board, which stores identification information of the needle tip so that a main device connected to the handpiece enables verification of whether or not the needle tip coupled to the handpiece is genuine and identifies the type of the needle tip.

Preferably, the skin treatment device further comprises a tip data storage on the connecting board, which counts the number of shots of the needles, wherein a main device receives information on the number of shots of the needles from the tip data storage, and stops using the needle tip coupled to the handpiece when the number of shots of the needles reaches a preset number.

Preferably, the motion trackable connector is a spring contact pin including a conducting tube coupled to one of the needle module and the connecting board, a contact pin enabling to slide up and down inside the conducting tube, which is made of a conductor and has a contact end electrically contacting the other one of the needle module and the connecting board, and a spring loaded in the conducting tube to elastically support the contact pin's sliding up and down, wherein in a state in which the contact end is in electrical contact with one of the needle module and the connecting board, as the needle module moves from the connecting board, the spring elastically supports the contact pin to maintain the electrical contact state of the contact end.

Preferably, the motion trackable connector is a flexible interconnector including a first terminal coupled and electrically connected to the needle module, a second terminal coupled and electrically connected to the connecting board, and a flexible conductor electrically interconnected between the first terminal and the second terminal, wherein in a state in which the flexible interconnector electrically connected to the needle module and the connecting board, as the needle module moves from the connecting board, the flexible conductor flexibly supports to maintain the electrical connection between the needle module and the connecting board.

Preferably, the motion trackable connector is a guided spring conductor including a spring guide having a guide body, a guide end fixed to the connecting board and a guide rod penetrated through the needle board so that the guide rod guides to motion of the needle module, and a conducting spring that is inserted into the guide body, an end of the conducting spring electrically contacts the connecting board, and the other end of the conducting spring electrically contacts the needle board so as to electrically connect between the connecting board and the needle board with elasticity of the conducting spring.

Preferably, the motion trackable connector is a frictional slide pin including a conducting barrel coupled and electrically connected to one of the needle module and the connecting board, a frictional slider enabling to slide up and down inside the conducting barrel, which is made of a conductor, wherein an end of the frictional slider is coupled and electrically connected to the other one of the needle module and the connecting board, and the other end of the frictional slider is positioned in the conducting barrel, and an elastic frictional contact provided on the other end of the frictional slider, which is elastically and electrically contact an inner surface of the conducting barrel, wherein in a state in which the needle module and the connecting board are electrically connected by the conducting barrel and the frictional slider, as the needle module moves from the connecting board, the elastic frictional contact elastically supports for the frictional slider to frictionally slide up and down inside the conducting barrel and maintains the electrical contact between the conducting barrel and the frictional slider.

Preferably, the motion trackable connector is a ball-point slide pin including a conducting barrel coupled and electrically connected to one of the needle module and the connecting board, a ball-point slider enabling to slide up and down inside the conducting barrel, which is made of a conductor, wherein an end of the frictional slider is coupled and electrically connected to the other one of the needle module and the connecting board, and the other end of the frictional slider is positioned in the conducting barrel, and a ball-point contact provided on the other end of the ball-point slider, which is electrically contact an inner surface of the conducting barrel, wherein in a state in which the needle module and the connecting board are electrically connected by the conducting barrel and the ball-point slider, as the needle module moves from the connecting board and the ball-point slider slides up and down inside the conducting barrel, the ball-point contact maintains the electrical contact between the conducting barrel and the ball-point slider.

Preferably, the motion trackable connector is an intermediate slide pin including a conducting barrel coupled and electrically connected to one of the needle module and the connecting board, a conducting slider enabling to slide up and down inside the conducting barrel, wherein an end of the conducting slider is coupled and electrically connected to the other one of the needle module and the connecting board, and the other end of the conducting slider is positioned in the conducting barrel, and a contact medium provided between the other end of the conducting slider and an inner surface of the conducting barrel so as to electrically contact between the conducting slider and the conducting barrel, wherein in a state in which the needle module and the connecting board are electrically connected by the conducting barrel and the conducting slider, as the needle module moves from the connecting board and the conducting slider slides up and down inside the conducting barrel, the contact medium maintains the electrical contact between the conducting barrel and the conducting slider.

According to an embodiment of the present invention, as the needle tip is mounted on the distal end of the handpiece, electrical connection with the handpiece can be made stably, and even if the needle module built in the needle tip performs linear reciprocating motions of extension and retraction by the driving device provided in the handpiece, the motion trackable connector provided in the needle tip can stably keep the electrical connection between the handpiece and the needle tip.

In addition, according to another embodiment of the present invention, only the needle tip certified as a genuine product can be coupled to the handpiece so that it can be used, and it is possible to enable the needle module in the needle tip to be used according to the allowable use limit that can be used stably and effectively.

DESCRIPTION OF THE PREFERRED EMBODIMENTS

The terms used in the present specification will be briefly described, and the present invention will be described in detail.

Terms used in the present invention have selected general terms currently widely used as possible while taking functions in the present invention into consideration, but this may vary depending on the intention or precedent of a technician engaged in the relevant field, the emergence of new technologies, and the like. In addition, in certain cases, there are terms arbitrarily selected by the applicant, and in this case, the meaning of the terms will be described in detail in the description of the corresponding invention. Therefore, the terms used in the present invention should be defined based on the meaning of the term and the overall contents of the present invention, not a simple name of the term.

When a part of the specification is said to "include" a certain element, it means that other elements may be further included rather than excluding other elements unless specifically stated to the contrary. In addition, terms such as "unit" and "module" described in the specification mean units that process at least one function or operation, which may be implemented as hardware or software, or as a combination of hardware and software.

Hereinafter, a skin treatment device according to embodiments of the present invention will be described in detail with reference to the drawings.

Figure 1:
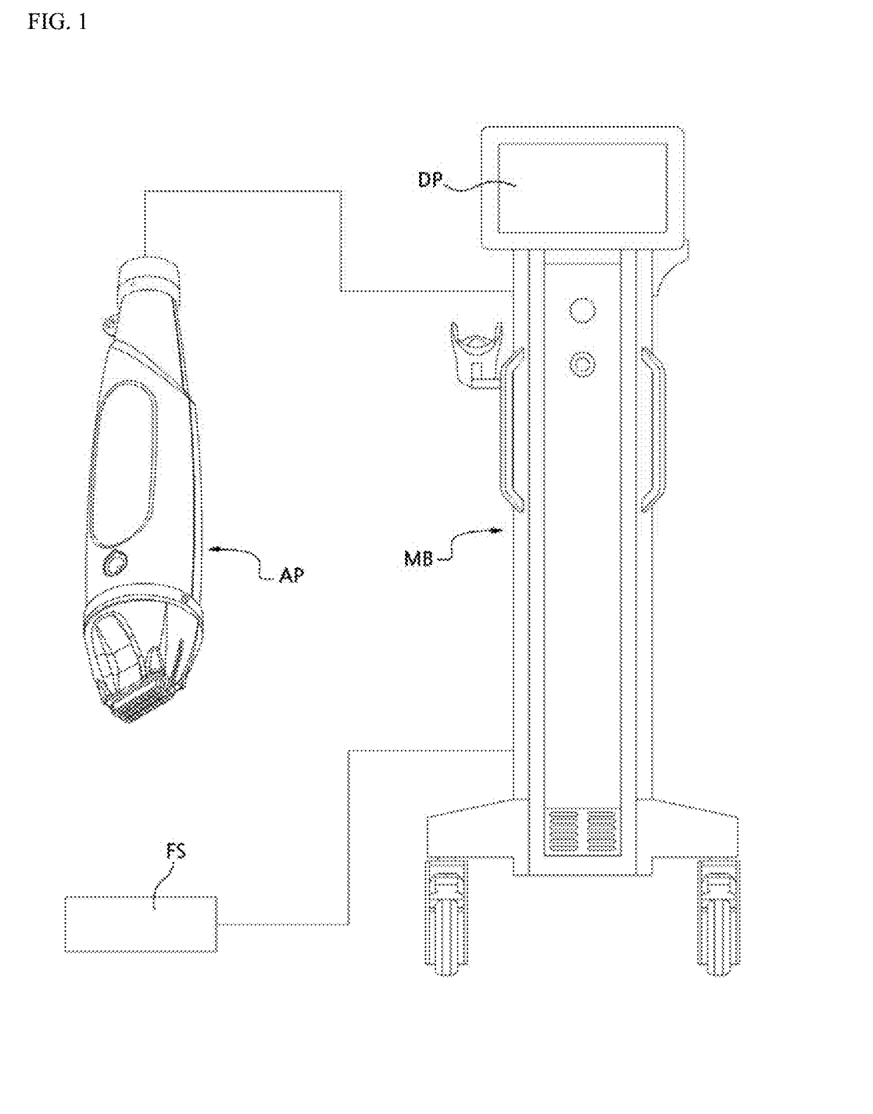
FIG. 1 shows a schematic configuration of a skin treatment device according to an embodiment of the present invention.

As shown in FIG. 1, the skin treatment device according to an embodiment of the present invention may include a main device MD, an applicator AP connected thereto, and a foot switch FS.

The practitioner may hold the applicator AP with his hand and perform skin treatment using the radio frequency (RF) with the applicator AP on the skin area of the patient.

When the practitioner puts his/her foot on the foot switch FS and puts the tip of the applicator AP on the patient's skin area, the micro-needles from the tip of the applicator AP can be inserted into the skin and treated by applying RF energy to the tissue in the skin through the micro-needles.

The main device MD may include a power supply, a device for generating RF energy for delivery to the applicator AP, that is, an RF generator, and a controller for controlling the RF generator. The main device MD may include a display device so that a practitioner can select or input various and selective parameters for skin treatment.

The controller may control the RF generator and the applicator AP so that controlled RF energy can be applied according to parameters selected through the display device.

Figure 2:
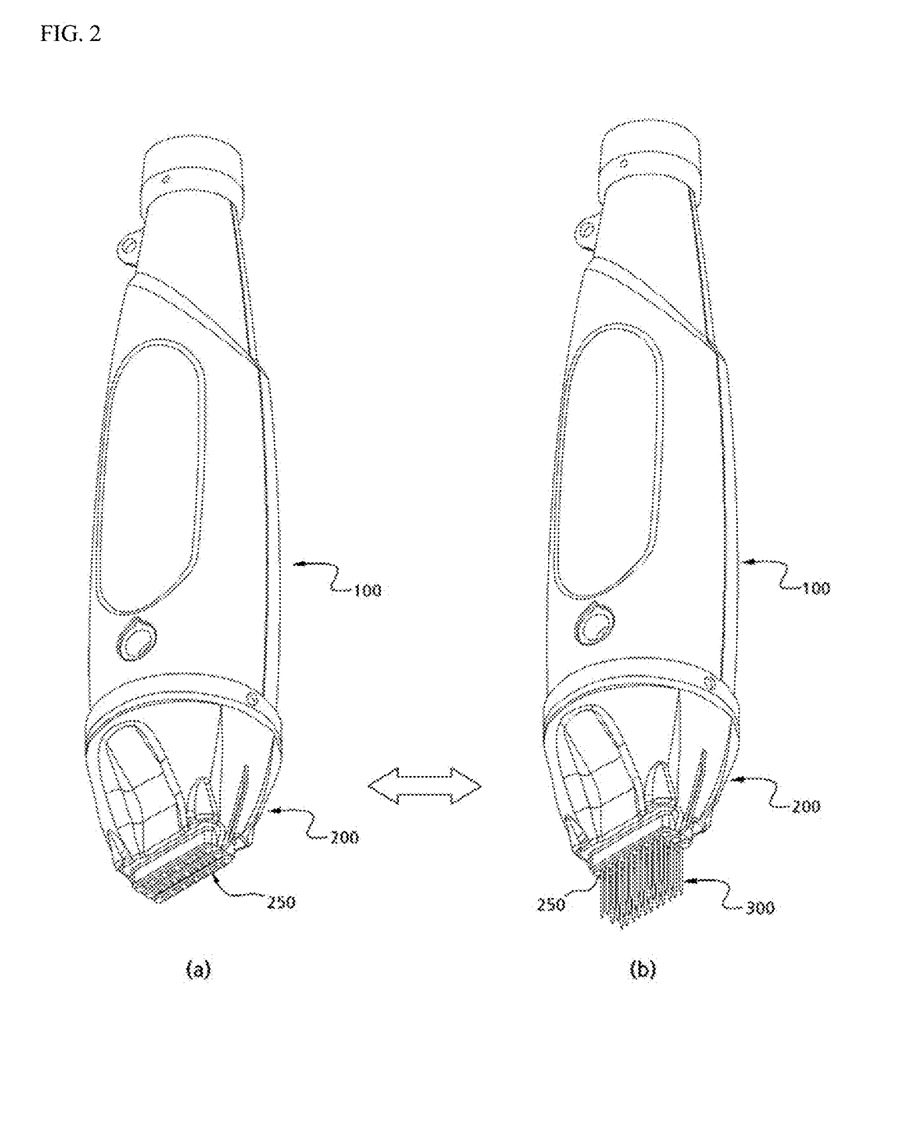
FIG. 2 shows extension and retraction of needles of an applicator of a skin treatment device according to an embodiment of the present invention, wherein (a) shows a state in which a plurality of needles are provided inside the needle tip, and (b) shows a state in which the plurality of needles are extended through the needle-holes.

More specifically, as shown in FIG. 2, the applicator AP may include a handpiece 100 constituting a body that a practitioner can hold by hand, and a needle tip 200 coupled to a distal end of the handpiece 100.

The needle tip 200 includes a plurality of micro-needles 300 to be inserted into the skin therein, and the distal end of the needle tip 200 has needle-holes 250 so that the micro-needles 300 in the needle tip 200 can penetrate through the needle-holes 250.

FIG. 2 (a) shows a state in which a plurality of needles 300 are provided inside the needle tip 200, FIG. 2 (b) shows a state in which the plurality of needles 300 in the needle tip 200 are extended through the needle-holes (250). When the practitioner steps on the foot switch, the plurality of needles 300 are extended and RF energy may be transmitted to the dermal tissue through the plurality of needles 300.

The handpiece 100 of the skin treatment device according to an embodiment of the present invention includes a motor therein. The motor can make the needles provided in the needle tip 200 be extended as shown in FIG. 2 (b), and can make the needles be retracted as shown in FIG. 2 (a).

Figure 3:
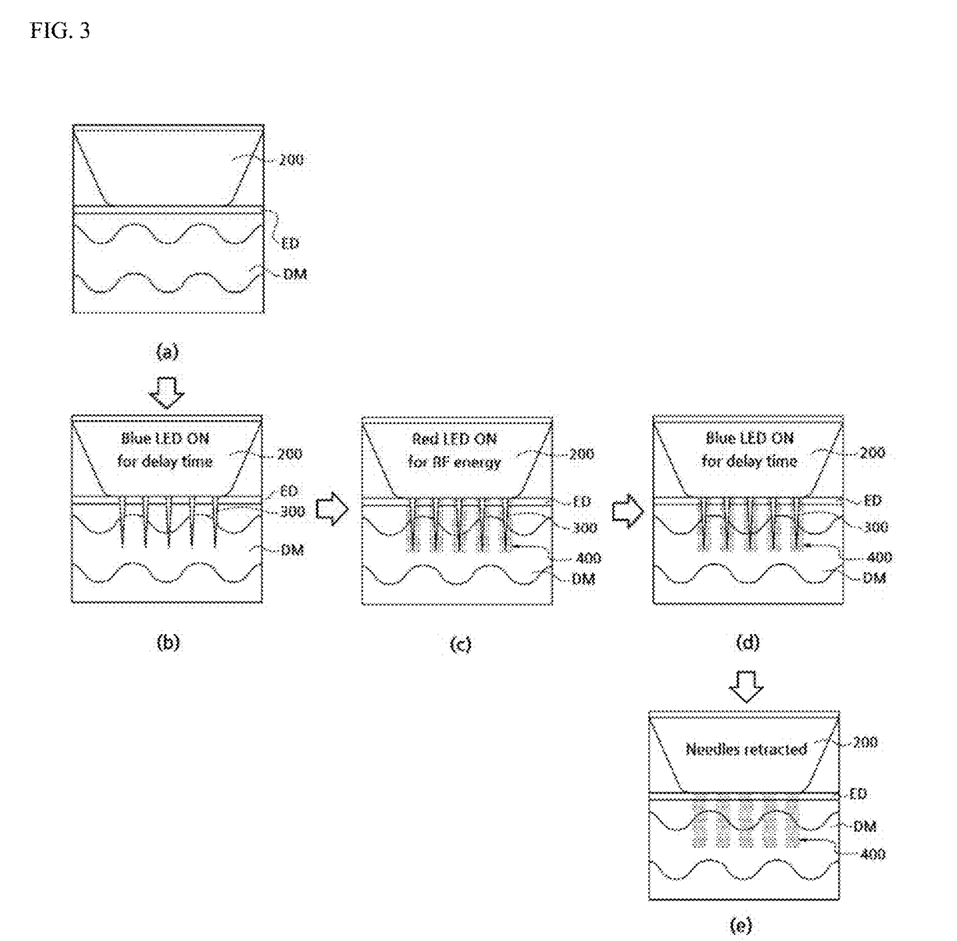
FIG. 3 shows a process in which a plurality of needles of the skin treatment device are operated in a state inserted into the skin according to an embodiment of the present invention, wherein (a) shows the needles which are inserted and located in the dermis DM, (b) shows the needles which stand-by for a preset delay time and the blue LED which is turned on, (c) shows the red LED which is turned on and the blue LED is turned off, (d) shows the blue LED which is turned on for the preset delay time and the red LED is turned off, and (e) shows the needles which are retracted.

FIG. 3 shows a process in which a plurality of needles 300 operate in a state inserted into the skin.

As shown in FIG. 3 (a), when the needle tip 200 of the applicator is in contact with the epidermis ED of the skin and the motor in the handpiece drive the needles 300 to be extended, the needles 300 are inserted and located in the dermis DM. Then, the needles 300 stand-by for a preset delay time, and the blue LED provided in the needle tip 200 is turned on (see FIG. 3(b)).

As soon as the preset delay time passes, high-frequency electricity is delivered to the plurality of needles 300 to deliver RF energy to the dermal tissue around the needles 300 so that the coagulation 400 is generated. While the RF energy is delivered to the dermal tissue, the red LED provided in the needle tip 200 is turned on and the blue LED is turned off (FIG. 3(*c*)).

After RF energy is delivered to the dermis (DM) for a preset time through the plurality of needles 300, the blue LED in the needle tip 200 is turned on while stand-by for a preset delay time again and the red LED is turned off (FIG. 3(*d*)).

When the delay time elapses in FIG. 3(*d*), the motor in the handpiece drives the needles 300 to be retracted so as to complete 'one shot' of the needles for skin treatment (FIG. 3(*e*)).

Figure 4:
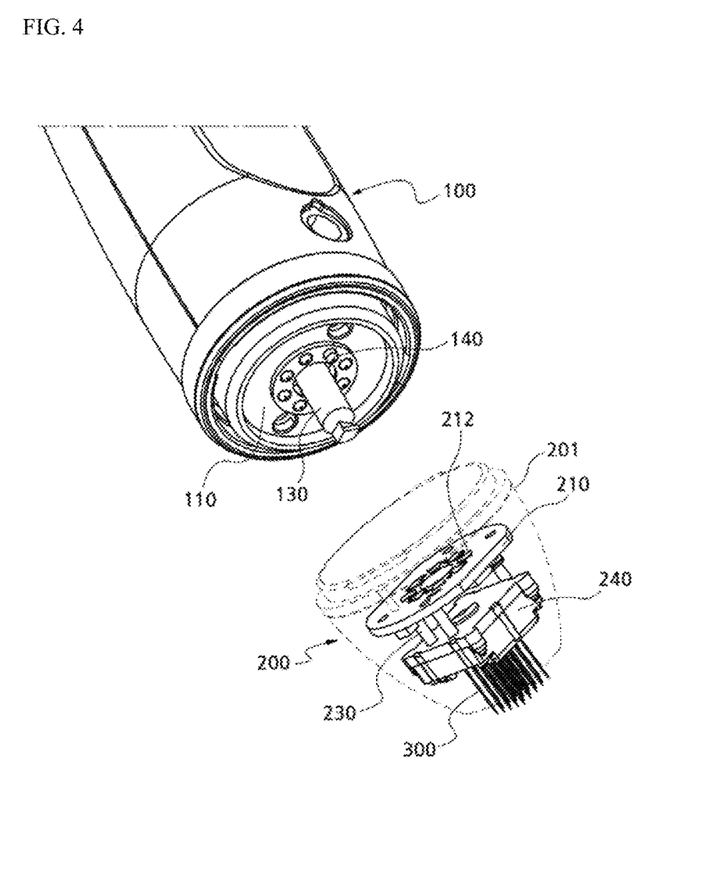
FIG. 4 shows the configuration of a state in which the handpiece and the needle tip are separated with respect to the applicator of the skin treatment device according to an embodiment of the present invention.
Figure 5:
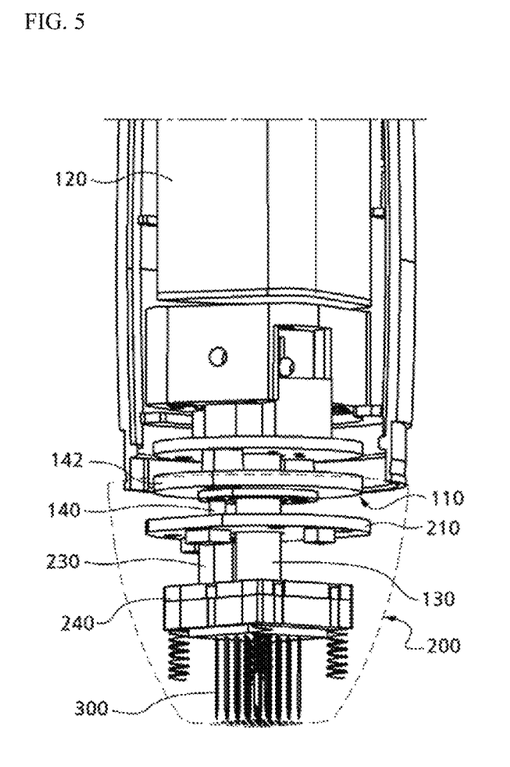
FIG. 5 shows the configuration of the handpiece and the needle tip coupled state with respect to the applicator of the skin treatment device according to an embodiment of the present invention.

Meanwhile, a configuration of a skin treatment device according to an embodiment of the present invention will be described with reference to FIGS. 4 and 5.

The applicator of the skin treatment device according to an embodiment of the present invention may be coupled to the distal end 110 of the handpiece 100 so that the needle tip 200 is detachably attached.

Since the micro-needles used in the skin treatment device is inserted into the skin of the human body, one needle tip cannot be used for several patients. In the skin treatment device according to an embodiment of the present invention, the needle tip should be detachable from the distal end of the handpiece.

The needle tip 200 includes a tip body 201 for protecting the needles 300 and the like provided therein, a connecting board 210 fixed to the inside of the tip body 201, and a needle module 240 in which a plurality of needles 300 are provided. The needle module 240 is linearly movable up and down by the motor in the handpiece. The connecting board 210 may be provided with a connecting terminal 212.

A drive shaft 130 is provided to be protruded from the distal end 110 of the handpiece 100 and driven up and down by the motor 120. An end board 142 is provided on distal end 110 of the handpiece 100 and electrically connected to the RF generator of the main device. A connector to tip 140 for electrically connecting to the needle tip 200 may be provided on the end board 142.

The connector to tip 140 may be provided as a component such as a plurality of POGO-Pins. POGO-pin is loaded with a spring therein so that an electrical connection can be made by contact with an external terminal.

When the needle tip 200 is coupled to the distal end 110 of the handpiece 100, the drive shaft 130 is coupled to the needle module 240, and the connector to tip 140 contacts connecting terminals 212 on the connecting board 210 for electrically connecting between the handpiece 100 and the needle tip 200.

Accordingly, the drive shaft 130 is coupled to the needle module 240 and linearly moves up and down according to the driving of the motor, so that the plurality of the needles can be extended from the tip body 201 or retracted into the tip body 201.

The motion trackable connector 230 is provided between the connecting board 210 and the needle module 240 so that RF power is transmitted from the connecting board 210 to the plurality of needles 300 through the motion trackable connector 230.

That is, the connector to tip 140 provided in the distal end 110 of the handpiece 100 is electrically contact with the connecting terminals 212 to deliver RF power from the RF generator of the main device to the connecting board 210. RF power is delivered from the connecting board 210 through the motion trackable connector 230 to the plurality of needles 300 of the needle module 240.

The motion trackable connector 230 can maintain the electrical connection between the connecting board 210 and the needle module 240 even if the needle module 240 is linearly moved up and down by the drive shaft 130.

The needle tip 200 coupled to the distal end 110 of the handpiece 100 is a consumable and should be discarded after skin treatment and replaced with a new one.

A tip data storage may be provided on the connecting board 210 provided in the needle tip 200. The tip data storage can store the identification information of the needle tip in which the tip data storage is installed, and the stored identification information of the needle tip is information that can certify that the needle tip is genuine (eg, an authentication code given in advance by the manufacturer of the needle tip). may include Accordingly, when the needle tip 200 is coupled to the distal end 110 of the handpiece 100, the controller of the main device reads the authentication code stored in the tip data storage to check whether the needle tip 200 is genuine.

There are several types of needle tips, and there are types according to the number of needles provided in the needle tips, types according to the arrangement, and those in which each needle is insulated and those in which each needle is not insulated.

The type of needle tip to be used can be determined depending on which part of the face or body of the patient for skin treatment is.

However, for example, if a different needle tip is accidentally used despite the fact that a predetermined needle tip should be used for a specific skin treatment, the specific skin treatment may be failed to a normal treatment. Therefore, according to the type of skin treatment, a needle tip suitable for it should be used.

The skin treatment device according to an embodiment of the present invention provides a method for allowing a needle tip suitable for a type of treatment to be used.

That is, the needle tip of the skin treatment device according to an embodiment of the present invention includes the tip data storage provided on the connecting board and the tip data storage may store information on the type of the corresponding needle tip.

Accordingly, when the needle tip 200 is coupled to the distal end 110 of the handpiece 100, the controller of the main device reads information about the type of the needle tip stored in the tip data storage and can identify what type of the needle tip 200 is.

The controller reads information about the type of needle tip stored in the tip data storage, checks whether the checked type of needle tip is a needle tip suitable for the skin treatment, and informs the practitioner if the wrong needle tip is combined to the handpiece.

Since the needle tip 200 performs a shot inserted into the skin using the plurality of needles 300, that is, micro-needles having a fine diameter, the needle may be bent or deformed according to long-term use. Accordingly, the needle tip 200 should be used for an appropriate number of shots.

However, there is a problem in that the practitioner cannot easily know whether the needle tip is used for an appropriate number of shots or whether the needle is deformed in the process of performing the skin treatment.

The skin treatment device according to an embodiment of the present invention may be determined whether the number of shots of the needle of the needle tip is appropriate, and when the appropriate number of shots is reached, an alarm may be provided so that a practitioner can replace the needle tip.

That is, as for the needle tip of the skin treatment device according to an embodiment of the present invention, the tip data storage provided on the connecting board counts the number of shots of the needle, and the controller determines whether the number of shots of the needle counted in the tip data storage is appropriate. Thus, it is possible to provide an alarm about whether the needle tip is replaced.

For example, an appropriate number of shots is predetermined for each type of needle tip, and information on the predetermined appropriate number of shots is stored in the tip data storage, and while counting the number of shots of the needles during treatment, if the counted number of shots of the needles reaches the predetermined number of appropriate shots, the controller can stop the operation of the needle tip and provide an alarm that the needle tip needs to be replaced.

That is, the controller or a processor provided in the needle tip records the number of shots in the tip data storage every time the needle tip makes a shot, and determines in real time whether the number of recorded shots reaches the preset number of shots, and when the number of recorded shots reaches the preset number of shots, it may provide an alarm that the needle tip needs to be replaced.

In the needle tip, a motion trackable connector that electrically connects between the connecting board and the needle module and maintains the electrical connection by tracking the movement of the needle module may be implemented in various structures and forms. Various embodiments of the motion trackable connector will be described with reference to FIGS. 6 to 11.

Figure 6:
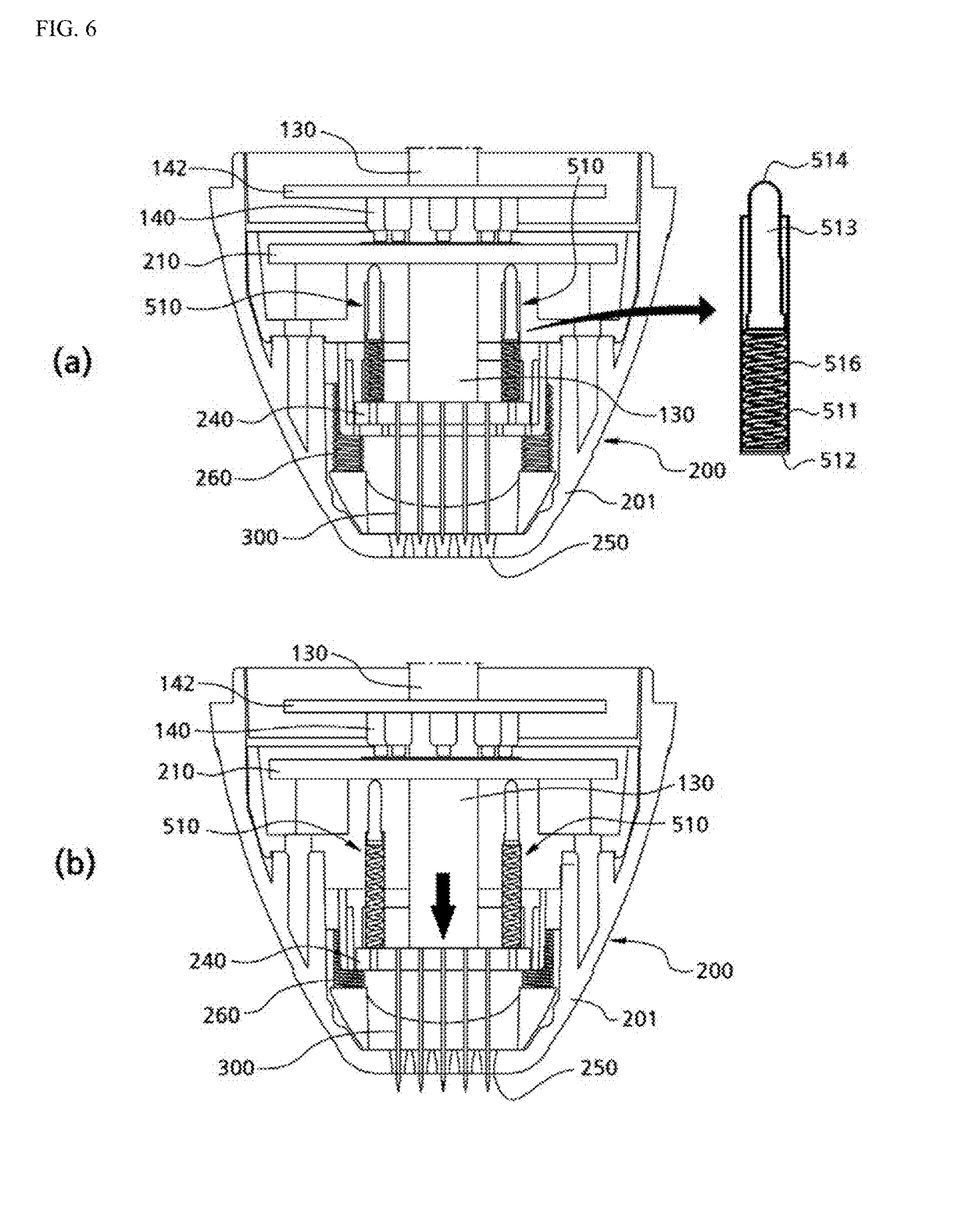
FIG. 6 shows that a spring contact pin is provided as a motion trackable connector in the needle tip of the skin treatment device according to an embodiment of the present invention, so that the electrical connection between the connecting board and the needle module is maintained by the spring contact pin according to the movement of the needle module wherein (a) shows a state in which the plurality of needles are retracted, and (b) shows a state in which the plurality of needles are extended.

FIG. 6 is a view showing a configuration in which the needle tip 200 is coupled to the distal end of the handpiece of the skin treatment device according to an embodiment of the present invention and the needle module 240 is linearly moved by the driving of the drive shaft 130.

FIG. 6 (a) shows a state in which the plurality of needles 300 are retracted, and FIG. 6 (b) shows a state in which the plurality of needles 300 are extended.

As shown in FIGS. 6 (a) and (b), the connector to tip 140 provided on the end board 142 is in electrical contact with the connecting terminals of the connecting board 210, RF power is transmitted from the connector to tip 140 of the end board 142 to the connecting board 210 through the connecting terminals.

As shown in FIGS. 6 (a) and (b), a spring contact pin 510 as an example of a motion trackable connector is provided between the needle module 240 and the connecting board 210.

The spring contact pin 510 may include a conducting tube 511 having a space therein, a spring 516 loaded in the inner space of the conducting tube 511, and a contact pin 513 that can slide up and down in the conducting tube 511 with elastic support by the spring 516.

It is preferable that the conducting tube 511, the spring 516, and the contact pin 513 all have conductive material.

The lower end 512 of the conducting tube 511 is coupled or fixed to the needle module 240 to conduct electricity with the plurality of needles 300 of the needle module 240, and the contact end 514 of the contact pin 513 can be made to electrically contact the contact terminals of the connecting board 210.

As shown in FIG. 6 (a), in the state in which the plurality of needles 300 are retracted, the spring 516 in the conducting tube 511 is in a compressed state, and according that the plurality of the needles 300 are extended as shown in FIG. 6 (b), the contact pin 513 slides by expansion of the spring 516 in the conducting tube 511 and the contact end 514 maintains contact with the contact terminals of the connecting board 210.

That is, even if the needle module 240 is moved up and down by the driving of the drive shaft 130 (even if the plurality of needles 300 repeat extension and retraction), the contact end 514 can be stably maintained in contact with the connecting board 210 because the spring 516 in the conducting tube 511 is elastically supporting the slide of the contact pin 513.

It is also possible that the lower end of the conducting tube 511 is coupled or fixed to the connecting board 210 to conduct electricity with the connecting board 210, and the contact end 514 of the contact pin 513 is electrically connected to the needle module 240 and the plurality of the needles 300.

Therefore, the spring contact pin 510 can electrically connect between the connecting board 210 and the needle module 240 while tracking the movement of the needle module 240 by supporting with the elastic force of the spring.

Figure 7:
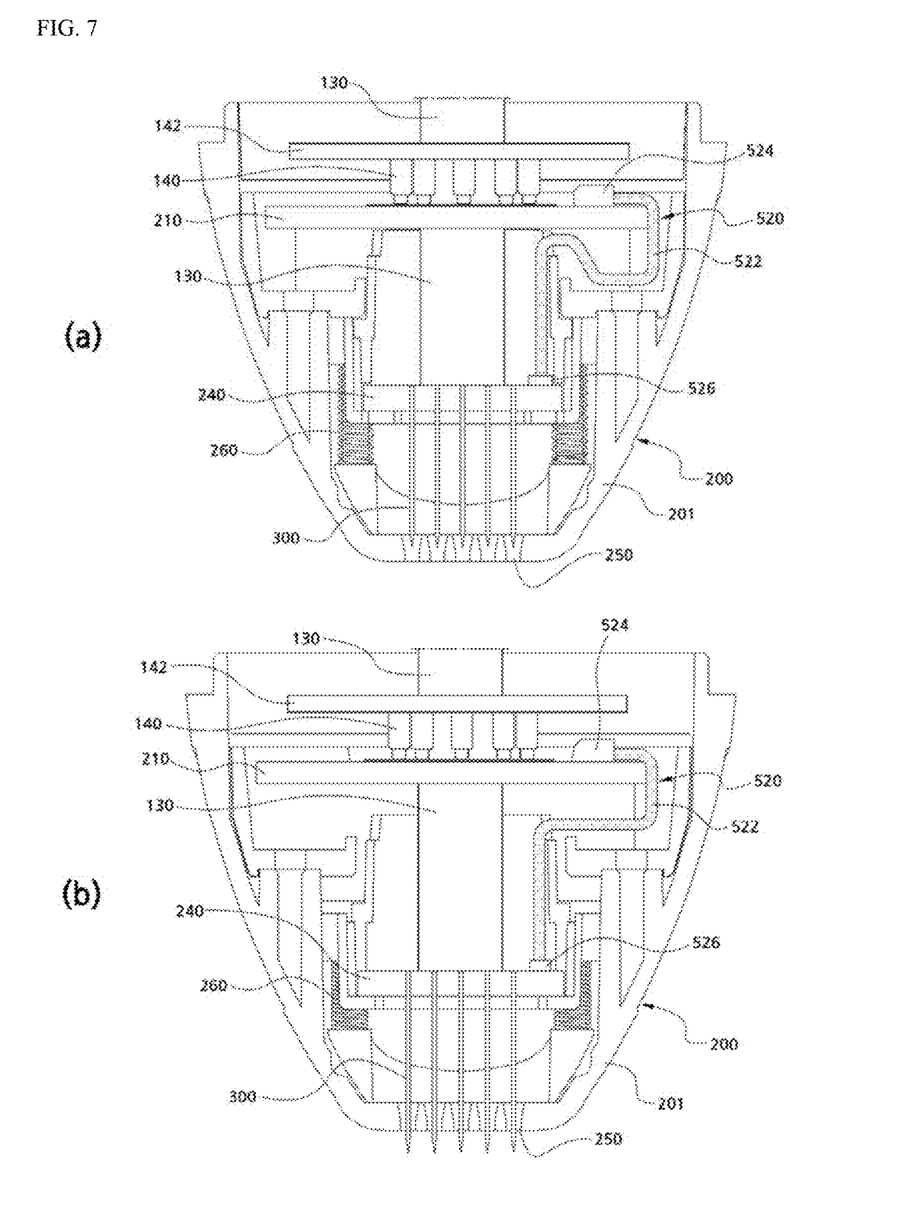
FIG. 7 shows that a flexible interconnector is provided as a motion trackable connector in the needle tip of the skin treatment device according to an embodiment of the present invention, so that the electrical connection between the connecting board and the needle module is maintained by the flexible interconnector according to the movement of the needle module, wherein (a) shows a state in which the plurality of needles are retracted, and (b) shows a state in which the plurality of needles are extended.

FIG. 7 is a view showing a configuration in which the needle tip 200 is coupled to the distal end of the handpiece of the skin treatment device according to an embodiment of the present invention and the needle module 240 is linearly moved by the driving of the drive shaft 130.

FIG. 7 (a) shows a state in which the plurality of needles 300 are retracted, and FIG. 7 (b) shows a state in which the plurality of needles 300 are extended.

As shown in FIGS. 7 (a) and (b), the connector to tip 140 provided on the end board 142 is in electrical contact with the connecting terminals of the connecting board 210, RF power is transmitted from the connector to tip 140 of the end board 142 to the connecting board 210 through the connecting terminals.

As shown in FIGS. 7 (a) and (b), a flexible interconnector 520 as an example of a motion trackable connector is provided between the needle module 240 and the connecting board 210.

The flexible interconnector 520 may include a first terminal 526 coupled and electrically connected to the needle module 240, a second terminal 524 coupled and electrically connected to the connecting board 210, and a flexible conductor 522 electrically connecting between the first terminal 526 and the second terminal 524, wherein the flexible conductor 522 has a flexible material to be easily bent.

The flexible interconnector 520 having the configuration as described above can allow the connecting board 210 and the needle module 240 to be electrically connected to each other.

That is, even if the needle module 240 is moved up and down by the driving of the drive shaft 130 (even if the plurality of needles 300 repeat extension and retraction), as the flexible conductor 522 is flexibly deformed, it is possible to maintain the electrical connection between the connecting board 210 and the needle module 240 through the first terminal 526 and the second terminal 524 (FIG. 7(a)) and (b)).

Therefore, the flexible interconnector 520 can electrically connect between the connecting board 210 and the needle module 240 while tracking the movement of the needle module 240 by flexibility of the flexible conductor 522.

Figure 8:
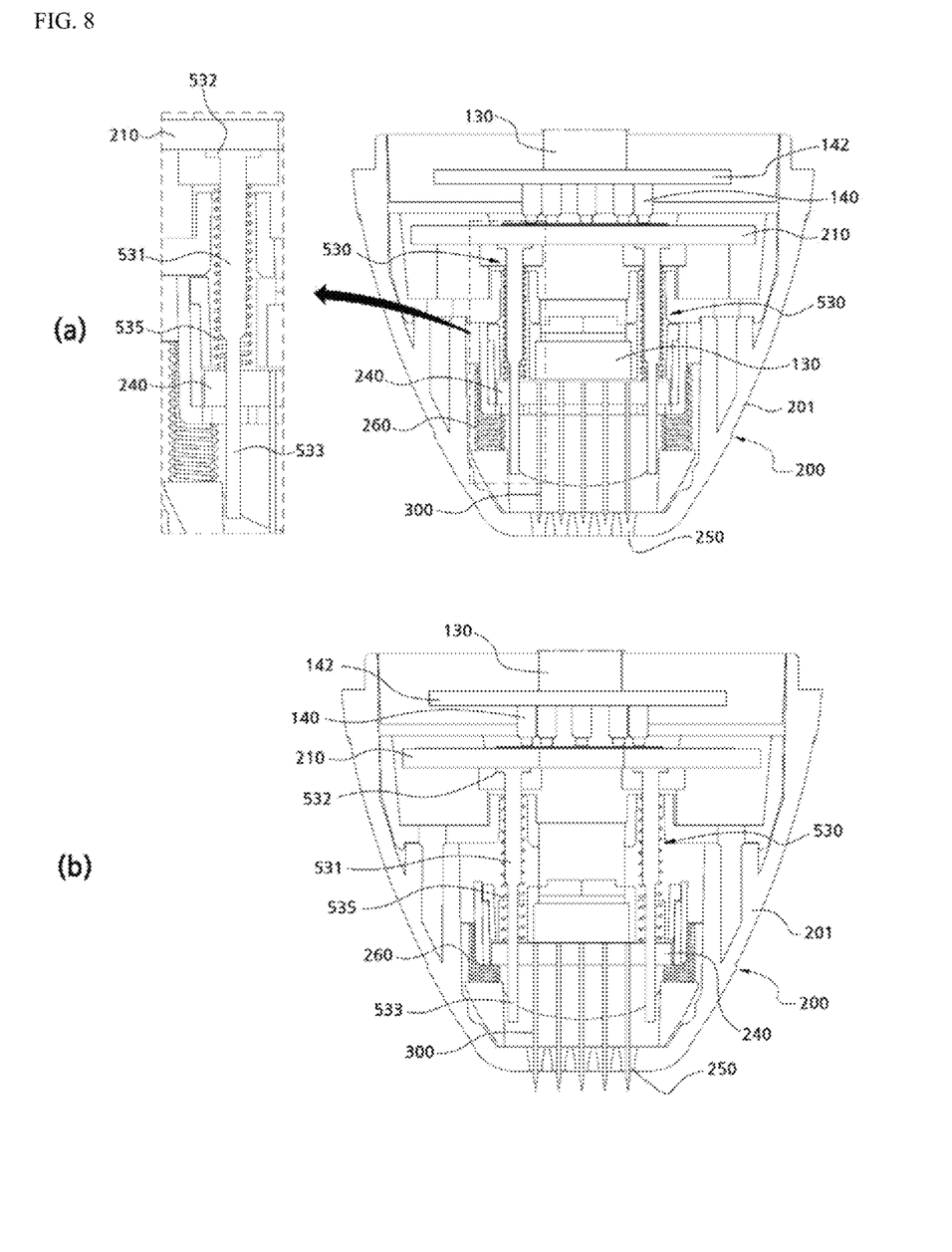
FIG. 8 shows that a guided spring conductor is provided as a motion trackable connector in the needle tip of the skin treatment device according to an embodiment of the present invention, so that the electrical connection between the connecting board and the needle module is maintained by the guided spring conductor according to the movement of the needle module, wherein (a) shows a state in which the plurality of needles are retracted, and (b) shows a state in which the plurality of needles 300 are extended.

FIG. 8 is a view showing a configuration in which the needle tip 200 is coupled to the distal end of the handpiece of the skin treatment device according to an embodiment of the present invention and the needle module 240 is linearly moved by the driving of the drive shaft 130.

FIG. 8 (a) shows a state in which the plurality of needles 300 are retracted, and FIG. 8 (b) shows a state in which the plurality of needles 300 are extended.

As shown in FIGS. 8 (a) and (b), the connector to tip 140 provided on the end board 142 is in electrical contact with the connecting terminals of the connecting board 210, RF power is transmitted from the connector to tip 140 of the end board 142 to the connecting board 210 through the connecting terminals.

As shown in FIGS. 8 (a) and (b), a guided spring conductor 530 as an example of a motion trackable connector is provided between the needle module 240 and the connecting board 210.

As shown in FIGS. 8 (a) and (b), the guided spring conductor 530 may include a spring guide 531, 532 and 533, and conducting spring 535.

The spring guide may include a guide body 531, a guide end 532 fixed to the connecting board 210 and a guide rod 533 penetrated through the needle module 240 so that the guide rod 533 guides to motion of the needle module 240.

The conducting spring 535 has a conductive material, which is inserted into the guide body 531 and is provided between the connecting board 210 and the needle module 240, and one end of the conducting spring 535 is electrically connected in contact with the connecting board (210), and the other end of the conducting spring 535 is electrically connected in contact with the needle module 240.

The guide rod 533 is formed to extend from the guide body 531, which penetrates the needle module 240 so that the needle module 531 is guided by the guide rod 533 to move up and down.

The conducting spring 535 is in a compressed state between the connecting board 210 and the needle module 240 to be electrically connected with each other.

As shown in FIG. 8 (a), in the state in which the plurality of needles 300 are retracted, the conducting spring 535 is in a compressed state, and according that the plurality of the needles 300 are extended as shown in FIG. 8 (b), both ends of the conducting spring 535 can keep in electrical contact with the connecting board 210 and the needle module 240, respectively by expansion of the conducting spring 535.

That is, even if the needle module 240 is moved up and down by the driving of the drive shaft 130 (even if the plurality of needles 300 repeat extension and retraction), the conducting spring 535 is stretched and contracted by elasticity while both ends of the conducting spring 535 maintain an electrical connection between the connecting board 210 and the needle module 240.

Therefore, the guided spring conductor 530 can electrically connect between the connecting board 210 and the needle module 240 while tracking the movement of the needle module 240 by supporting with the elastic force of the conducting spring.

Figure 9:
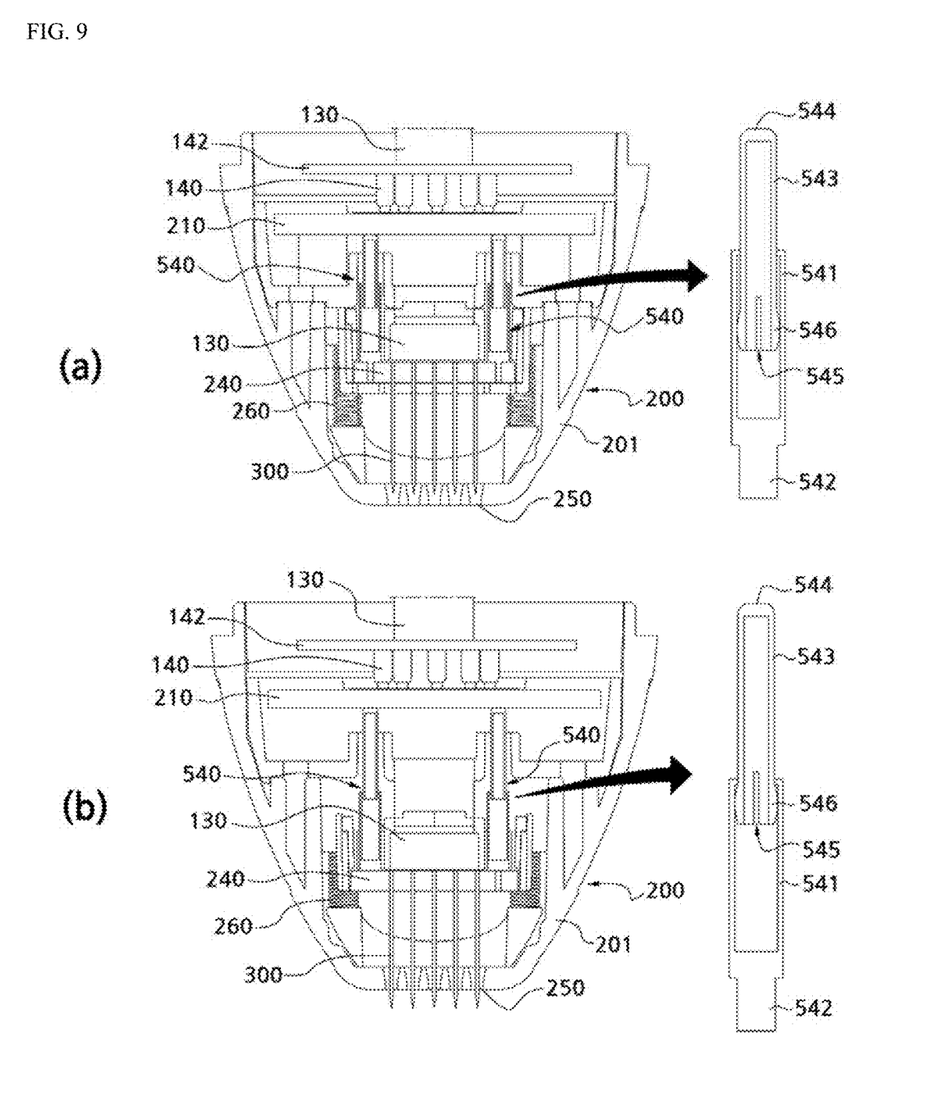
FIG. 9 shows that a frictional slide pin is provided as a motion trackable connector in the needle tip of the skin treatment device according to an embodiment of the present invention, so that the electrical connection between the connecting board and the needle module is maintained by the frictional slide pin according to the movement of the needle module, wherein (a) shows a state in which the plurality of needles are retracted, and (b) shows a state in which the plurality of needles are extended.

FIG. 9 is a view showing a configuration in which the needle tip 200 is coupled to the distal end of the handpiece of the skin treatment device according to an embodiment of the present invention and the needle module 240 is linearly moved by the driving of the drive shaft 130.

FIG. 9 (a) shows a state in which the plurality of needles 300 are retracted, and FIG. 9 (b) shows a state in which the plurality of needles 300 are extended.

As shown in FIGS. 9 (a) and (b), the connector to tip 140 provided on the end board 142 is in electrical contact with the connecting terminals of the connecting board 210, RF power is transmitted from the connector to tip 140 of the end board 142 to the connecting board 210 through the connecting terminals.

As shown in FIGS. 9 (a) and (b), a frictional slide pin 540 as an example of a motion trackable connector is provided between the needle module 240 and the connecting board 210.

The frictional slide pin 540 may include a conducting barrel 541 having a space therein, and a frictional slider 543 that can slide up and down in the conducting barrel 541.

It is preferable that the conducting barrel 541 and the frictional slider 543 all have conductive material.

The lower end 542 of the conducting barrel 541 is fixed to the needle module 240 to electrically connect with the plurality of needles 300 of the needle module 240, and the end portion 544 of the frictional slider 543 is fixed to the connecting board 210 to electrically connect with the connector to tip 140.

It is also possible that the lower end of the conducting barrel 541 is fixed to the connecting board 210 to electrically connect with the connector to tip 140, and the end portion 544 of the frictional slider 543 to electrically connect with the needles 300.

An elastic frictional contact 546 may be provided in a portion 545 in the conducting barrel of the frictional slider 543 to be in elastic and electrical contact with the inner surface of the conducting barrel 541.

When the needle module 240 moves down while the elastic frictional contact 546 provided in the frictional slider 543 is in close contact with the inner surface of the conducting barrel 541 elastically and electrically, the elastic frictional contact 546 keeps electrical connection between the frictional slider 543 and the conducting barrel 541 while the frictional slider 543 slides frictionally on the inner surface of the conducting barrel (541).

That is, even if the needle module 240 is moved up and down by the driving of the drive shaft 130 (even if the plurality of needles 300 repeat extension and retraction), the elastic frictional contact 546 of the frictional slider 543 in the conducting barrel 541 maintains electrical contact, thereby maintaining the electrical connection between the connecting board 210 and the needle module 240.

Therefore, the frictional slide pin 540 can electrically connect between the connecting board 210 and the needle module 240 while tracking the movement of the needle module 240 by the frictionally slide operation.

Figure 10:
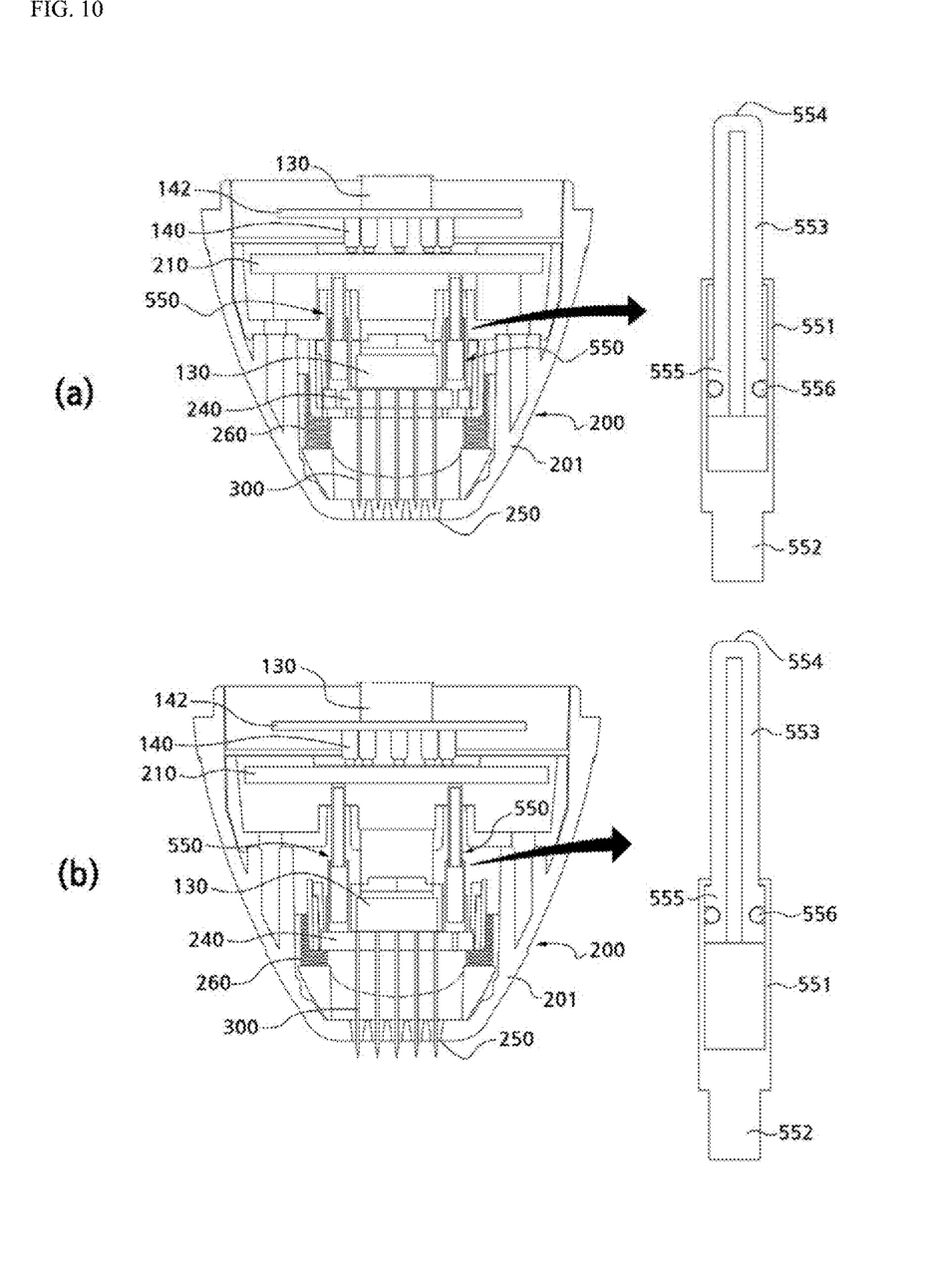
FIG. 10 shows that a ball-point slide pin is provided as a motion trackable connector in the needle tip of the skin treatment device according to an embodiment of the present invention, so that the electrical connection between the connecting board and the needle module is maintained by the ball-point slide pin according to the movement of the needle module, wherein (a) shows a state in which the plurality of needles are retracted, and (b) shows a state in which the plurality of needles are extended.

FIG. 10 is a view showing a configuration in which the needle tip 200 is coupled to the distal end of the handpiece of the skin treatment device according to an embodiment of the present invention and the needle module 240 is linearly moved by the driving of the drive shaft 130.

FIG. 10 (a) shows a state in which the plurality of needles 300 are retracted, and FIG. 10 (b) shows a state in which the plurality of needles 300 are extended.

As shown in FIGS. 10 (a) and (b), the connector to tip 140 provided on the end board 142 is in electrical contact with the connecting terminals of the connecting board 210, RF power is transmitted from the connector to tip 140 of the end board 142 to the connecting board 210 through the connecting terminals.

As shown in FIGS. 10 (a) and (b), a ball-point slide pin 550 as an example of a motion trackable connector is provided between the needle module 240 and the connecting board 210.

The ball-point slide pin 550 may include a conducting barrel 551 having a space therein, and a ball-point slider 553 that can slide up and down in the conducting barrel 551.

It is preferable that the conducting barrel 551 and the ball-point slider 553 all have conductive material.

The lower end 552 of the conducting barrel 551 is fixed to the needle module 240 to electrically connect with the plurality of needles 300 of the needle module 240, and the end portion 554 of the ball-point slider 553 is fixed to the connecting board 210 to electrically connect with the connector to tip 140.

It is also possible that the lower end of the conducting barrel 551 is fixed to the connecting board 210 to electrically connect with the connector to tip 140, and the end portion 554 of the ball-point slider 553 to electrically connect with the needles 300.

A ball-point contact 556 may be provided in a portion 555 in the conducting barrel of the ball-point slider 553 to be in elastic and electrical contact with the inner surface of the conducting barrel 551.

When the needle module 240 moves down while the ball-point contact 556 provided in the ball-point slider 553 is in contact with the inner surface of the conducting barrel 541 electrically, the ball-point contact 556 keeps electrical connection between the ball-point slider 553 and the conducting barrel 551 while the ball-point slider 553 is sliding and the ball-point contact 556 are rolling on the inner surface of the conducting barrel 551.

That is, even if the needle module 240 is moved up and down by the driving of the drive shaft 130 (even if the plurality of needles 300 repeat extension and retraction), the ball-point contact 556 of the ball-point slider 553 in the conducting barrel 551 maintains electrical contact, thereby maintaining the electrical connection between the connecting board 210 and the needle module 240.

Therefore, the ball-point slide pin 550 can electrically connect between the connecting board 210 and the needle module 240 while tracking the movement of the needle module 240 by sliding with ball-rolling.

Figure 11:
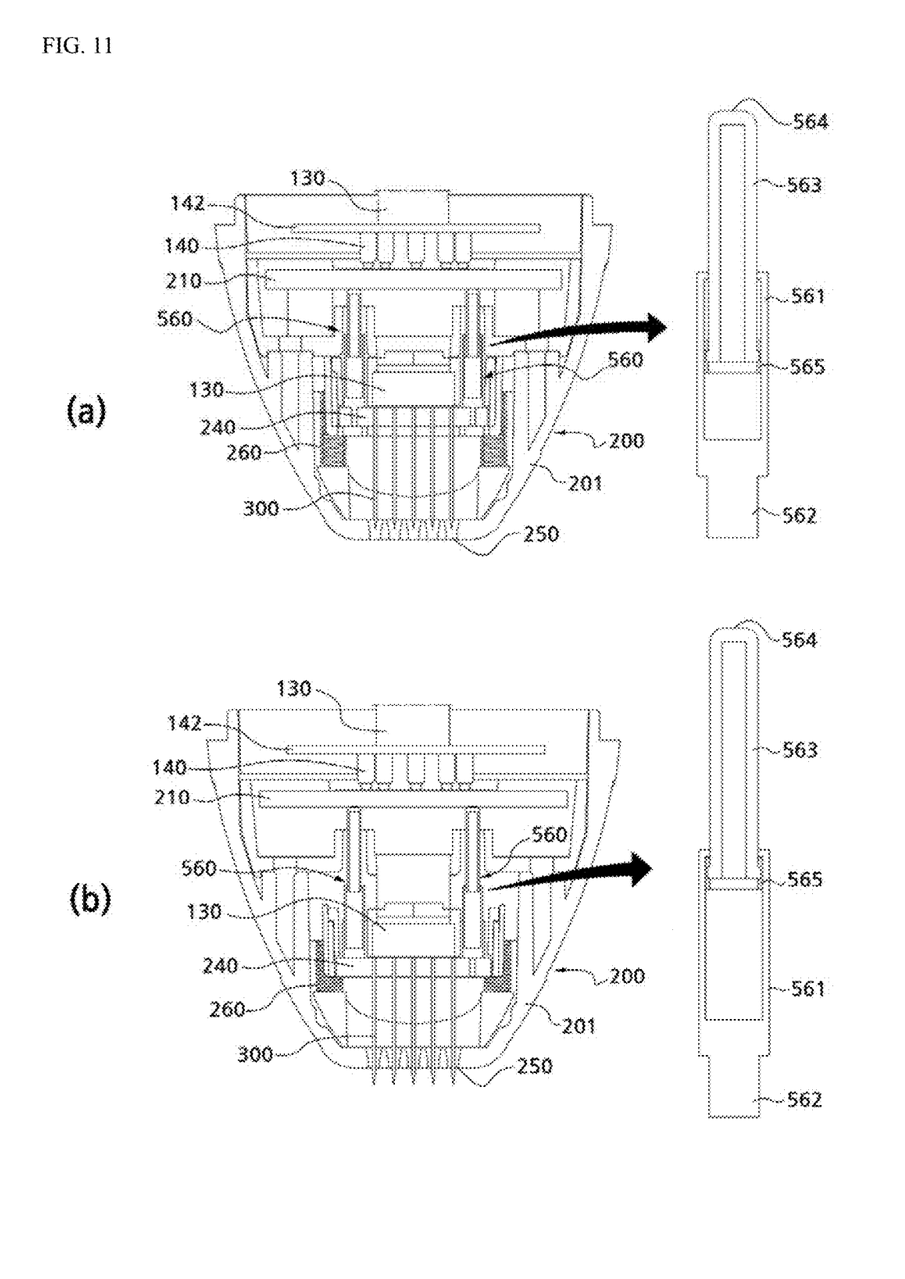
FIG. 11 shows that an intermediate slide pin is provided as a motion trackable connector in the needle tip of the skin treatment device according to an embodiment of the present invention, so that the electrical connection between the connecting board and the needle module is maintained by the intermediate slide pin according to the movement of the needle module, wherein (a) shows a state in which the plurality of needles are retracted, and (b) shows a state in which the plurality of needles are extended.

FIG. 11 is a view showing a configuration in which the needle tip 200 is coupled to the distal end of the handpiece of the skin treatment device according to an embodiment of the present invention and the needle module 240 is linearly moved by the driving of the drive shaft 130.

FIG. 11 (a) shows a state in which the plurality of needles 300 are retracted, and FIG. 11 (b) shows a state in which the plurality of needles 300 are extended.

As shown in FIGS. 11 (a) and (b), the connector to tip 140 provided on the end board 142 is in electrical contact with the connecting terminals of the connecting board 210, RF power is transmitted from the connector to tip 140 of the end board 142 to the connecting board 210 through the connecting terminals.

As shown in FIGS. 11 (a) and (b), an intermediate slide pin 560 as an example of a motion trackable connector is provided between the needle module 240 and the connecting board 210.

The intermediate slide pin 560 may include a conducting barrel 561 having a space therein, and a conducting slider 563 that can slide up and down in the conducting barrel 561.

It is preferable that the conducting barrel 561 and the conducting slider 563 all have conductive material.

The lower end 562 of the conducting barrel 561 is fixed to the needle module 240 to electrically connect with the plurality of needles 300 of the needle module 240, and the end portion 564 of the conducting slider 563 is fixed to the connecting board 210 to electrically connect with the connector to tip 140.

It is also possible that the lower end of the conducting barrel 561 is fixed to the connecting board 210 to electrically connect with the connector to tip 140, and the end portion 564 of the conducting slider 563 to electrically connect with the needles 300.

A contact medium 565 may be provided between conducting slider 563 and the inner surface of the conducting barrel 561 and electrically connect with each other. The contact medium 565 may be coupled to the conducting slider 563.

When the needle module 240 moves down while the contact medium 565 provided in the conducting slider 563 is in contact with the inner surface of the conducting barrel 561 electrically, the contact medium 565 keeps electrical connection between the conducting slider 563 and the conducting barrel 561 while the conducting slider 563 is sliding and the contact medium 566 is frictionally sliding on the inner surface of the conducting barrel 561.

That is, even if the needle module 240 is moved up and down by the driving of the drive shaft 130 (even if the plurality of needles 300 repeat extension and retraction), the contact medium 565 of the conducting slider 563 in the conducting barrel 561 maintains electrical contact, thereby maintaining the electrical connection between the connecting board 210 and the needle module 240.

Therefore, the intermediate slide pin 560 can electrically connect between the connecting board 210 and the needle module 240 while tracking the movement of the needle module 240 by sliding with contact medium.

As stated above, the skin treatment device according to an embodiment of the present invention, as the needle tip is mounted on the distal end of the handpiece, electrical connection with the handpiece can be made stably, and even if the needle module built in the needle tip performs linear reciprocating motions of extension and retraction by the driving device provided in the handpiece, the motion trackable connector provided in the needle tip can stably keep the electrical connection between the handpiece and the needle tip.

What is claimed is:

1. A skin treatment device comprising:
   a handpiece including a motor to move a driving shaft linearly therein and having a distal end from which the driving shaft is protruded, wherein a connector to tip is provided on the distal end; and
   a needle tip comprising:
      a tip body configured to be detachably coupled to the distal end of the handpiece and have needle-holes through which a plurality of needles move;
      a needle module including a needle board coupled to the driving shaft and the plurality of needles electrically connected to the needle board, wherein the needle module linearly moves by the driving shaft for the needles to be extended and retracted through the needle-holes;
      a connecting board having connecting conductors to electrically contact with the connector to tip of the handpiece by coupling with the tip body and the distal end of the handpiece; and
      a motion trackable connector configured to electrically connect with the connecting board and the needle module so that RF energy is delivered from the connecting board to the needle module, and keep the electrical connection trackable to motion of the needle module during extension and retraction of the needles.

2. The skin treatment device according to claim 1, wherein the connecting board includes a through hole through which the driving shaft passes and is coupled to the needle module.

3. The skin treatment device according to claim 1, further comprising a tip data storage on the connecting board, which stores identification information of the needle tip so that a main device connected to the handpiece enables verification of whether or not the needle tip coupled to the handpiece is genuine and identifies the type of the needle tip.

4. The skin treatment device according to claim 1, further comprising a tip data storage on the connecting board, which counts the number of shots of the needles, wherein a main device receives information on the number of shots of the needles from the tip data storage, and stops using the needle tip coupled to the handpiece when the number of shots of the needles reaches a preset number.

5. The skin treatment device according to claim 1, wherein the motion trackable connector is a spring contact pin including:
   a conducting tube coupled to one of the needle module and the connecting board;
   a contact pin enabled to slide up and down inside the conducting tube, which is made of a conductor and has a contact end electrically contacting the other one of the needle module and the connecting board; and
   a spring loaded in the conducting tube to elastically support the contact pin's sliding up and down,
   wherein in a state in which the contact end is in electrical contact with one of the needle module and the connecting board, as the needle module moves from the connecting board, the spring elastically supports the contact pin to maintain the electrical contact state of the contact end.

6. The skin treatment device according to claim 1, wherein the motion trackable connector is a flexible interconnector including:
   a first terminal coupled and electrically connected to the needle module;
   a second terminal coupled and electrically connected to the connecting board; and
   a flexible conductor electrically interconnected between the first terminal and the second terminal,
   wherein in a state in which the flexible interconnector electrically connected to the needle module and the connecting board, as the needle module moves from the connecting board, the flexible conductor flexibly supports to maintain the electrical connection between the needle module and the connecting board.

7. The skin treatment device according to claim 1, wherein the motion trackable connector is a guided spring conductor including:
   a spring guide having a guide body, a guide end fixed to the connecting board and a guide rod penetrated through the needle board; and
   a conducting spring that is inserted into the guide body, an end of the conducting spring electrically contacts the connecting board, and the other end of the conducting spring electrically contacts the needle board so as to electrically connect between the connecting board and the needle board with elasticity of the conducting spring.

8. The skin treatment device according to claim 1, wherein the motion trackable connector is a frictional slide pin including:
   a conducting barrel coupled and electrically connected to one of the needle module and the connecting board;
   a frictional slider enabled to slide up and down inside the conducting barrel, which is made of a conductor, wherein an end of the frictional slider is coupled and electrically connected to the other one of the needle module and the connecting board, and the other end of the frictional slider is positioned in the conducting barrel; and
   an elastic frictional contact provided on the other end of the frictional slider, which is elastically and electrically in contact with an inner surface of the conducting barrel,
   wherein in a state in which the needle module and the connecting board are electrically connected by the conducting barrel and the frictional slider, as the needle module moves from the connecting board, the elastic frictional contact elastically supports the frictional slider to frictionally slide up and down inside the conducting barrel and maintains the electrical contact between the conducting barrel and the frictional slider.

9. The skin treatment device according to claim 1, wherein the motion trackable connector is a ball-point slide pin including:
   a conducting barrel coupled and electrically connected to one of the needle module and the connecting board;
   a ball-point slider enabled to slide up and down inside the conducting barrel, which is made of a conductor, wherein an end of the frictional slider is coupled and electrically connected to the other one of the needle module and the connecting board, and the other end of the frictional slider is positioned in the conducting barrel; and
   a ball-point contact provided on the other end of the ball-point slider, which is electrically in contact with an inner surface of the conducting barrel,
   wherein in a state in which the needle module and the connecting board are electrically connected by the conducting barrel and the ball-point slider, as the needle module moves from the connecting board and the ball-point slider slides up and down inside the conducting barrel, the ball-point contact maintains the electrical contact between the conducting barrel and the ball-point slider.

10. The skin treatment device according to claim 1, wherein the motion trackable connector is an intermediate slide pin including:
   a conducting barrel coupled and electrically connected to one of the needle module and the connecting board;
   a conducting slider enabled to slide up and down inside the conducting barrel, wherein an end of the conducting slider is coupled and electrically connected to the other one of the needle module and the connecting board, and the other end of the conducting slider is positioned in the conducting barrel; and
   a contact medium provided between the other end of the conducting slider and an inner surface of the conducting barrel so as to electrically contact between the conducting slider and the conducting barrel,
   wherein in a state in which the needle module and the connecting board are electrically connected by the conducting barrel and the conducting slider, as the needle module moves from the connecting board and the conducting slider slides up and down inside the conducting barrel, the contact medium maintains the electrical contact between the conducting barrel and the conducting slider.

* * * * *